United States Patent
Pizzamiglio et al.

(10) Patent No.: US 6,844,455 B2
(45) Date of Patent: Jan. 18, 2005

(54) PROCESS FOR THE PREPARATION OF ANTHRACYCLINE DERIVATIVES

(75) Inventors: Valentina Pizzamiglio, S. Fiorano (IT); Walter Cabri, Rozzano (IT); Elio Mapelli, Melzo (IT)

(73) Assignee: Antibioticos S.p.A., Rodano (IT)

( * ) Notice: Subject to any disclaimer, the term of this patent is extended or adjusted under 35 U.S.C. 154(b) by 186 days.

(21) Appl. No.: 10/276,823

(22) PCT Filed: May 10, 2001

(86) PCT No.: PCT/EP01/05304

§ 371 (c)(1),
(2), (4) Date: Dec. 19, 2002

(87) PCT Pub. No.: WO01/87814

PCT Pub. Date: Nov. 22, 2001

(65) Prior Publication Data

US 2004/0044189 A1 Mar. 4, 2004

(30) Foreign Application Priority Data

May 19, 2000 (IT) .................................... MI2000A1122

(51) Int. Cl.[7] .............................................. C07C 49/00

(52) U.S. Cl. ....................................................... 552/202
(58) Field of Search .......................................... 552/202

(56) References Cited

FOREIGN PATENT DOCUMENTS

| EP | 0 337 665 | 10/1989 |
|---|---|---|
| GB | 2 215 332 | 9/1989 |

*Primary Examiner*—Barbara P. Badio
(74) *Attorney, Agent, or Firm*—Rothwell, Figg, Ernst & Manbeck, P.C.

(57) ABSTRACT

The present invention discloses a process for the semi-synthesis of 4-demethoxydaunomycinone, (8s-cis)-acetyl-10-hydroxy-7,8,9,10-tetrahydro-6,8,11-trihydroxy-5,12-naphthacenedione, of formula (I).

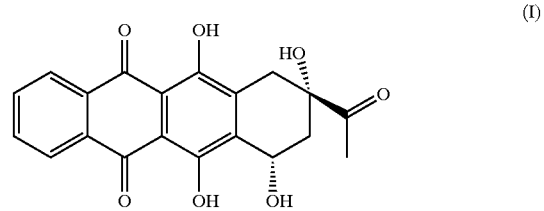

6 Claims, No Drawings

PROCESS FOR THE PREPARATION OF ANTHRACYCLINE DERIVATIVES

The present invention relates to a process for the semi-synthesis of 4-demethoxydaunomycinone, (8s-cis)-acetyl-10-hydroxy-7,8,9,10-tetrahydro-6,8,11-trihydroxy-5,12-naphthacenedione, of formula (I):

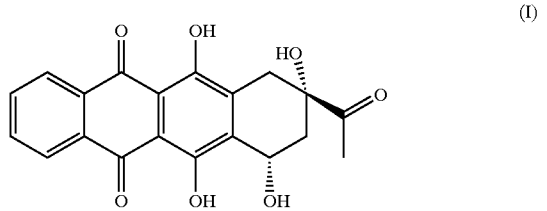

(I)

4-Demethoxydaunomycinone is a key intermediate for the synthesis of antitumoral anthracyclines such as Idarubicin (Penco S., Chim. Ind. 1993, 75, 369; Ganzina F., Pacciarini M. A., Di Pietro N., Invest New Drugs 1986, 4, 85). Furthermore, said intermediate can be used in the preparation of products under advanced study such as Annamycin (Horton D., Priebe W., Varela O. Carbohydrate research 1984, 130, C1–C3) and MEN 10755 (WO 95/09173).

Idarubicin is used in the treatment of leukemias in both adults and children and it is also active on solid tumors, for example breast tumors. This anthracycline exerts the same effects as doxorubicin on tumors and leukemias, but it can be administered at lower dosages and induces reduced side effects. Idarubicin has further been found to have higher affinity to lipids than other the anthracyclines and may therefore be administered orally, which makes Idarubicin the choice anthracycline for the clinical treatment of tumors and leukemias in children.

Total syntheses of 4-demethoxydaunomycinone based on Friedel-Craft and Diels-Alder type reactions are described in literature. Said synthesis generally involves a high number of steps, drastic conditions and very low global yields.

Two processes for the semi-synthesis of 4-demethoxydaunomycinone starting from daunomycinone are also known. The first, disclosed in U.S. Pat. No. 5,015,745, leads to demethoxylation of daunomycinone in six steps: demethylation at the 4-position, protection of the C13 ketone, sulfonation of the C4 hydroxyl, amination with a secondary amine, deprotection of the amine, diazotation and hydrolysis of the diazonium to give 4-demethoxydaunomycinone. Said process, however, provides low yield (11.5%), and also comprises a reductive diazotation step which involves safety problems from the industrial standpoint.

The second semi-synthesis process, disclosed in U.S. Pat. No. 5,103,029, comprises the 5 following steps, starting from daunomycinone (Figure, (a)–(e)):

(a) demethylation at –4,
(b) protection of the C13 ketone,
(c) sulfonation of the C4 hydroxyl,
(d) reduction of the sulfonate
(e) deprotection to give 4-demethoxydaunomycinone.

The protection of the C13 ketone has been to date considered a critical step in that the active sulfonic precursor used for the sulfonation of the C4 hydroxyl is recognizedly able to react with the keto groups giving raise to enolsulfonates. It has now surprisingly been found that the sulfonation reaction of the C4 phenol does not damage the C13 keto group even when said group is not protected.

Therefore, the present invention relates to a process for the preparation of 4-demethoxydaunomycinone, which comprises:

1) reacting 4-hydroxydaunomycinone of formula (II)

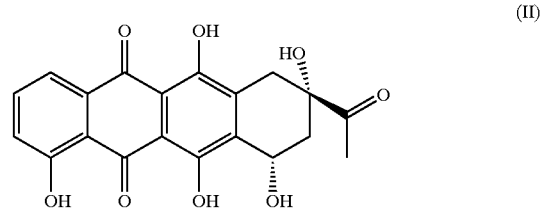

(II)

in the presence of N,N-diisopropylethylamine and 4-dimethylaminopyridine, with compounds of formula (III)

$$RSO_2X \quad \text{(III)}$$

wherein X is a group capable of reacting with a phenol to give a sulfonate, and is preferably selected from halogen, $OSO_2R$, imidazolyl, $NH(C_6H_5)(RSO_2)$; R is an alkyl group having 1 to 10 carbon atoms optionally substituted with one or more halogen atoms, preferably a trifluoromethyl group, or aryl optionally substituted with halogen, alkyl, alkoxy or nitro groups;

2) reducing the resulting 4-demethyl-daunomycinone sulfonate of formula (IV)

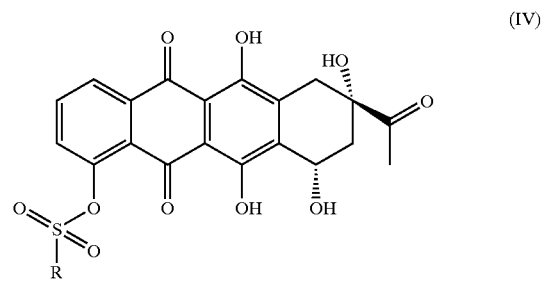

(IV)

in the presence of catalytic amounts of compounds of formula (V)

$$ML_nL'_m \quad \text{(V)}$$

wherein M is a transition metal atom, L and L' can be the same or different and are an anion or a neutral molecule and m and n can range from 0 to 4.

The starting product 4-demethyl-daunomycinone (carminomycinone, II) can be obtained by reacting (+) daunomycinone with $AlCl_3$ in chlorinated solvent under reflux. (+) Daunomycinone can in its turn be obtained by suitable hydrolysis of daunorubicin. Carminomycinone is subsequently be subjected to sulfonation using a suitable active sulfonic precursor in the presence of N,N-diisopropylethylamine and dimethylaminopyridine and solvents. According to a preferred embodiment, carminomycinone (II) is subjected to triflation with trifluoromethanesulfonic anhydride.

The resulting sulfonate derivative is directly reduced at the 4-demethoxydaunorubicin aglycon in inert solvent with catalytic amounts of compounds of formula $ML_nL'_m$, wherein M, L, L', m and n are as defined above. Preferred metals for the reduction reaction are palladium and nickel, whereas the ligands (L) can be Cl⁻, $CH_3COO^-$, or neutral molecules as solvents, mono- or diphosphines, phosphites or diamines. The transition metal/ligand molar ratio usually ranges from 1:1 to 1:4. The compound $ML_nL'_m$ is preferably 1,1'-bis(diphenylphosphino)ferrocene.

The catalyst can be prepared in situ starting from suitable precursors, in the presence of hydrogen donors, such as trialkylammonium formate obtained by addition of formic acid to trialkylamine. The reduction reaction is carried out at a temperature ranging from 0 to 150° C., but it usually ranges from 20 to 100° C., for a time ranging from 4 to 24 hours, preferably 6 to 18 hours. The catalyst to sulfonate ratios are comprised from 1:1 to 1:1000, preferably from 1:20 to 1:100.

The process of the present invention provides a number of advantages. First of all, the intermediate of formula (IV), which is a further object of the present invention, proved to be more stable to the aromatization of the A ring than the corresponding intermediate ketalized at the 13-position. Furthermore, the steps necessary for the preparation of the final product have been reduced from 5 to 3 compared with the process disclosed in U.S. Pat. No. 5,103,029, as the carminoderivative carbonyl protection step (Figure, (b)), and the deprotection step of the same carbonyl after reduction (Figure, (e)) are no longer necessary. In this way, the overall yield remarkably increases while reducing the environmental impaction. It should, in fact, be noted that the protection step involves the use of toluene under reflux (110° C.) and of ethylene glycol, being the latter very harmful upon acute expositions and involving serious health risks in case of ingestion. Furthermore, the deprotection step involves the use of strong acids such as trifluoroacetic acid or concentrated hydrochloric acid in tetrahydrofuran.

DESCRIPTION OF THE FIGURE

Steps (a), (b'), (c'): synthetic scheme according to the present invention; steps (a)–(e): synthetic scheme according to U.S. Pat. No. 5,103,029.

The following examples illustrate the present invention in greater detail.

EXAMPLE 1

4-Demethyl-4-trifluoromethanesulfonyl-daunomycinone

To a solution of 4-demethyl-4-hydroxydaunomycinone (28.6 g, 68 mmoles) in 1500 ml of pyridine, cooled to 0–5° C., diisopropylethylamine (49 ml, 500 mmoles) and dimethylaminopyridine (11 g, 108.8 mmoles) were added. To the resulting mixture, kept at 0–5° C., trifluoromethanesulfonic anhydride (25 ml, 170 mmoles) was added dropwise. After 1 hour of stirring in the cold, the mixture was poured into 400 ml of cold 10% HCl and extracted with $CH_2Cl_2$ (4000 ml×2). The combined organic phases were washed with 0.1N HCl (400 ml) and then with $H_2O$ (600 ml×2). The organic phase was evaporated to dryness and the residue was taken up in absolute ethanol (200 ml), then filtered to obtain 22.7 g of crystal (65% recovery).

EXAMPLE 2

4-Demethoxydaunomycinone

A solution of triethylamine (6.2 ml, 0.045 moles), 99% formic acid (1.5 ml, 0.04 moles), dioxane (31.3 ml), 1,1'bis-(diphenylphosphino)ferrocene (0.9 g, 0.0005 moles), $Pd(OAc)_2$ (0.11 g, 0.0005 moles) was prepared under nitrogen stream. The solution was heated to 40° C. to a red colour, then a suspension of 4-demethyl-4-trifluoromethanesulfonyl-daunomicynone (6.2 g, 0.012 moles) in dioxane (124 ml) was slowly added dropwise. After completion of the reaction, the mixture was poured into $CH_2Cl_2$ (620 ml), washed with NaOH (1.25 g/l, 250 ml×3) and subsequently with $H_2O$ (500 ml). The organic phase was separated and concentrated to small volume. Methanol (50 ml) and 1N HCl (50 ml) were added. The crystal was left under stirring for 30', then filtered, washed with $H_2O$ (30 ml) and dried under vacuum at 40° C. to constant weight, to obtain 3.29 g of crystal (66% recovery).

EXAMPLE 3

4-Demethoxydaunomycinone

A solution of triethylamine (6.2 ml, 0.045 moles), 99% formic acid (1.5 ml, 0.04 moles), DMF (31.3 ml), 1,1' bis-(diphenylphosphino)ferrocene (0.29 g, 0.0005 moles), $Pd(OAc)_2$ (0.11 g, 0.0005 moles) was prepared under nitrogen stream. The solution was heated to 40° C. to red colour. A suspension of 4-demethyl-4-trifluoromethanesulfonyl-daunomycinone (6.2 g, 0.012 moles) in dimethylformamide (124 ml) was very slowly added dropwise. After completion of the reaction, the mixture was poured in $CH_2Cl_2$ (620 ml), washed with NaOH (1.25 g/l, 250 ml×3) and with $H_2O$ (500 ml). The organic phase was separated and concentrated to small volume. Methanol (50 ml) and 1N HCl (50 ml) were added. The crystal was left under stirring for 30', then filtered, washed with $H_2O$ (30 ml) and dried under vacuum at 40° C. to constant weight, to obtain 2.9 g of crystal (58% recovery).

What is claimed is:

1. A process for the preparation of 4-demethoxydaunomycinone, which comprises:

a) reacting 4-hydroxydaunomycinone of formula (II)

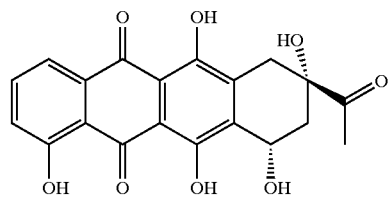

(II)

in the presence of N,N-diisopropylethylamine and 4-dimethylaminopyridine, with compounds of formula (III)

$RSO_2X$ (III)

wherein:

X is selected from halogen, $OSO_2R$, imidazolyl, $NH(C_6H_5)(RSO_2)$, R is a trifluoromethyl group;

b) reducing the resulting 4-demethyl-daunomycinone sulfonate of formula (IV)

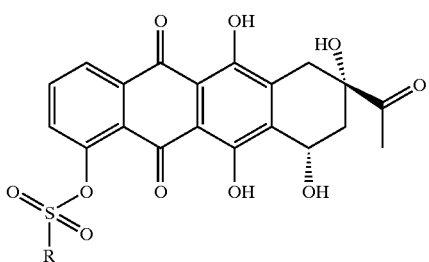

(IV)

in the presence of catalytic amounts of compounds of formula (V)

$$ML_nL'_m \quad (V)$$

wherein:
M is a transition metal atom,
L and L' can be the same or different and are an anion or a neutral molecule, and
m and n can range from 0 to 4.

2. A process as claimed in claim 1, in which the metal M of compound (V) is selected from Pd and Ni, ligands L are selected from Cl⁻, CH₃COO⁻, neutral molecules, mono/diphosphines, phosphites and diamines, the transition metal/ligand molar ratio ranges from 1:1 to 1:4.

3. A process as claimed in claim 2, in which ligands L is 1,1'-bis(diphenylphosphino)ferrocene.

4. A process as claimed in claim 1, in which the reaction temperature of step (b) ranges from 20 to 100° C.

5. A process as claimed in claim 1, in which the ratio of catalyst to sulfonate ranges from 1:20 to 1:100.

6. A compound of formula (IV)

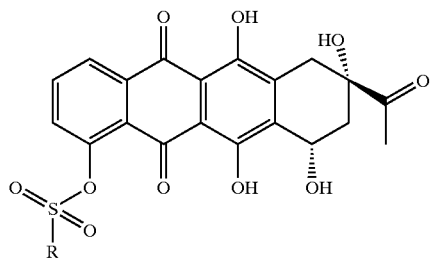

(IV)

wherein R is trifluoromethyl.

* * * * *